（12）United States Patent
De Groot

(10) Patent No.: US 7,812,963 B2
(45) Date of Patent: Oct. 12, 2010

(54) INTERFEROMETRY METHOD FOR ELLIPSOMETRY, REFLECTOMETRY, AND SCATTEROMETRY MEASUREMENTS, INCLUDING CHARACTERIZATION OF THIN FILM STRUCTURES

(75) Inventor: Peter J. De Groot, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 0 days.

(21) Appl. No.: 12/173,972

(22) Filed: Jul. 16, 2008

(65) Prior Publication Data

US 2009/0015844 A1  Jan. 15, 2009

Related U.S. Application Data

(63) Continuation of application No. 11/760,163, filed on Jun. 8, 2007, now Pat. No. 7,403,289, which is a continuation of application No. 11/542,617, filed on Oct. 3, 2006, now Pat. No. 7,315,382, which is a continuation of application No. 10/659,060, filed on Sep. 9, 2003, now Pat. No. 7,139,081.

(60) Provisional application No. 60/409,147, filed on Sep. 9, 2002, provisional application No. 60/452,615, filed on Mar. 6, 2003, provisional application No. 60/478,300, filed on Jun. 13, 2003.

(51) Int. Cl.
    *G01B 11/02*   (2006.01)
(52) U.S. Cl. .................................. 356/497
(58) Field of Classification Search ............... 356/497, 356/511–516, 485, 489, 495
    See application file for complete search history.

(56) References Cited

U.S. PATENT DOCUMENTS

| 2,612,074 A |   | 9/1952  | Mirau              |         |
|-------------|---|---------|--------------------|---------|
| 4,188,122 A |   | 2/1980  | Massie et al.      |         |
| 4,199,219 A |   | 4/1980  | Suzki et al.       |         |
| 4,340,306 A | * | 7/1982  | Balasubramanian    | 356/513 |
| 4,355,903 A |   | 10/1982 | Sandercock         |         |
| 4,523,846 A |   | 6/1985  | Breckinridge et al.|         |

(Continued)

FOREIGN PATENT DOCUMENTS

DE          4108944        9/1992

(Continued)

OTHER PUBLICATIONS

US 7,151,607, 12/2008, De Groot et al. (withdrawn).

(Continued)

*Primary Examiner*—Gregory J Toatley, Jr.
*Assistant Examiner*—Scott M Richey
(74) *Attorney, Agent, or Firm*—Fish & Richardson P.C.

(57) ABSTRACT

A method including: imaging test light emerging from a test object over a range of angles to interfere with reference light on a detector, wherein the test and reference light are derived from a common source; for each of the angles, simultaneously varying an optical path length difference from the source to the detector between interfering portions of the test and reference light at a rate that depends on the angle at which the test light emerges from the test object; and determining an angle-dependence of an optical property of the test object based on the interference between the test and reference light as the optical path length difference is varied for each of the angles.

34 Claims, 7 Drawing Sheets

U.S. PATENT DOCUMENTS

| | | |
|---|---|---|
| 4,576,479 A | 3/1986 | Downs |
| 4,583,858 A | 4/1986 | Lebling et al. |
| 4,618,262 A | 10/1986 | Maydan et al. |
| 4,639,139 A | 1/1987 | Wyant et al. |
| 4,660,980 A | 4/1987 | Takabayashi et al. |
| 4,710,642 A | 12/1987 | McNeil |
| 4,806,018 A | 2/1989 | Falk |
| 4,818,110 A | 4/1989 | Davidson |
| 4,869,593 A | 9/1989 | Biegen |
| 4,923,301 A | 5/1990 | White |
| 4,948,253 A * | 8/1990 | Biegen ................. 356/495 |
| 4,964,726 A | 10/1990 | Kleinknecht et al. |
| 4,999,014 A | 3/1991 | Gold et al. |
| 5,042,949 A | 8/1991 | Greenberg et al. |
| 5,042,951 A | 8/1991 | Gold et al. |
| 5,073,018 A | 12/1991 | Kino et al. |
| 5,112,129 A | 5/1992 | Davidson et al. |
| 5,129,724 A | 7/1992 | Brophy et al. |
| 5,133,601 A | 7/1992 | Cohen et al. |
| 5,135,307 A | 8/1992 | de Groot et al. |
| 5,153,669 A | 10/1992 | DeGroot |
| 5,164,790 A | 11/1992 | McNeil et al. |
| 5,166,751 A | 11/1992 | Massig |
| 5,173,746 A | 12/1992 | Brophy |
| 5,194,918 A | 3/1993 | Kino et al. |
| 5,241,369 A | 8/1993 | McNeil et al. |
| 5,301,010 A | 4/1994 | Jones et al. |
| 5,355,221 A | 10/1994 | Cohen et al. |
| 5,384,717 A | 1/1995 | Ebenstein |
| 5,386,119 A | 1/1995 | Ledger |
| 5,390,023 A | 2/1995 | Biegen |
| 5,398,113 A | 3/1995 | de Groot |
| 5,402,234 A | 3/1995 | Deck |
| 5,459,564 A | 10/1995 | Chivers |
| 5,471,303 A | 11/1995 | Ai et al. |
| 5,481,811 A | 1/1996 | Smith |
| 5,483,064 A | 1/1996 | Frey et al. |
| 5,539,517 A | 7/1996 | Cabib et al. |
| 5,543,841 A | 8/1996 | Kanamori |
| 5,555,471 A | 9/1996 | Xu et al. |
| 5,587,792 A | 12/1996 | Nishizawa et al. |
| 5,589,938 A | 12/1996 | Deck |
| 5,602,643 A | 2/1997 | Barrett |
| 5,633,714 A | 5/1997 | Nyyssonen |
| 5,640,270 A | 6/1997 | Aziz et al. |
| 5,703,692 A | 12/1997 | McNeil et al. |
| 5,757,502 A | 5/1998 | Weling |
| 5,774,224 A | 6/1998 | Kerstens |
| 5,777,740 A | 7/1998 | Lacey et al. |
| 5,777,742 A | 7/1998 | Marron |
| 5,784,164 A * | 7/1998 | Deck et al. ............... 356/511 |
| 5,856,871 A | 1/1999 | Cabib et al. |
| 5,867,276 A | 2/1999 | McNeil et al. |
| 5,880,838 A | 3/1999 | Marx et al. |
| 5,900,633 A | 5/1999 | Solomon et al. |
| 5,912,741 A | 6/1999 | Carter et al. |
| 5,923,423 A | 7/1999 | Sawatari et al. |
| 5,943,134 A | 8/1999 | Yamaguchi et al. |
| 5,953,124 A | 9/1999 | Deck |
| 5,956,141 A * | 9/1999 | Hayashi ................. 356/496 |
| 5,959,735 A | 9/1999 | Maris et al. |
| 5,963,329 A | 10/1999 | Conrad et al. |
| 6,028,670 A | 2/2000 | Deck |
| 6,160,621 A | 12/2000 | Perry et al. |
| 6,172,452 B1 | 1/2001 | Itaya et al. |
| 6,172,752 B1 | 1/2001 | Haruna et al. |
| 6,242,739 B1 | 6/2001 | Cherkassky |
| 6,249,351 B1 | 6/2001 | de Groot |
| H1972 H | 7/2001 | Inoue |
| 6,259,521 B1 | 7/2001 | Miller et al. |
| 6,275,297 B1 | 8/2001 | Zalicki |
| 6,377,349 B1 * | 4/2002 | Fercher ................. 356/497 |
| 6,381,009 B1 | 4/2002 | McGahan |
| 6,392,749 B1 | 5/2002 | Meeks et al. |
| 6,417,109 B1 | 7/2002 | Jordan et al. |
| 6,429,943 B1 | 8/2002 | Opsal et al. |
| 6,449,048 B1 | 9/2002 | Olszak |
| 6,449,066 B1 | 9/2002 | Arns et al. |
| 6,483,580 B1 | 11/2002 | Xu et al. |
| 6,500,591 B1 | 12/2002 | Adams |
| 6,507,405 B1 | 1/2003 | Grek et al. |
| 6,525,825 B2 | 2/2003 | de Groot |
| 6,545,761 B1 | 4/2003 | Aziz et al. |
| 6,545,763 B1 | 4/2003 | Kim et al. |
| 6,590,656 B2 | 7/2003 | Xu et al. |
| 6,597,460 B2 | 7/2003 | Groot et al. |
| 6,611,330 B2 | 8/2003 | Lee et al. |
| 6,624,894 B2 | 9/2003 | Olszak et al. |
| 6,633,389 B1 | 10/2003 | Poris et al. |
| 6,633,831 B2 | 10/2003 | Nikoonahad et al. |
| 6,636,322 B1 | 10/2003 | Terashita |
| 6,694,284 B1 | 2/2004 | Nikoonahad et al. |
| 6,714,307 B2 | 3/2004 | De Groot et al. |
| 6,721,094 B1 | 4/2004 | Sinclair et al. |
| 6,741,357 B2 | 5/2004 | Wang et al. |
| 6,741,360 B2 | 5/2004 | D'Agraives |
| 6,775,006 B2 | 8/2004 | De Groot et al. |
| 6,775,009 B2 | 8/2004 | Hill |
| 6,798,511 B1 | 9/2004 | Zhan et al. |
| 6,822,745 B2 | 11/2004 | De Groot et al. |
| 6,856,384 B1 | 2/2005 | Rovira |
| 6,888,638 B1 | 5/2005 | Hill |
| 6,891,627 B1 | 5/2005 | Levy et al. |
| 6,909,509 B2 | 6/2005 | De Groot |
| 6,925,860 B1 | 8/2005 | Poris et al. |
| 6,940,604 B2 | 9/2005 | Jung et al. |
| 6,956,658 B2 | 10/2005 | Meeks et al. |
| 6,956,660 B2 | 10/2005 | Meeks et al. |
| 6,985,232 B2 | 1/2006 | Sezginer |
| 6,989,905 B2 | 1/2006 | De Groot |
| 6,999,180 B1 | 2/2006 | Janik et al. |
| 7,012,700 B2 | 3/2006 | de Groot et al. |
| 7,018,271 B2 | 3/2006 | Wiswesser et al. |
| 7,038,850 B2 | 5/2006 | Chang et al. |
| 7,046,371 B2 | 5/2006 | De Lega et al. |
| 7,061,623 B2 | 6/2006 | Davidson |
| 7,068,376 B2 | 6/2006 | De Groot |
| 7,088,451 B2 | 8/2006 | Sezginer |
| 7,102,761 B2 | 9/2006 | De Lega et al. |
| 7,106,454 B2 | 9/2006 | De Groot et al. |
| 7,119,909 B2 | 10/2006 | Unruh et al. |
| 7,139,081 B2 | 11/2006 | de Groot |
| 7,139,083 B2 | 11/2006 | Fielden et al. |
| 7,142,311 B2 | 11/2006 | De Lega |
| 7,177,030 B2 | 2/2007 | Leizerson et al. |
| 7,205,518 B2 | 4/2007 | Neuvonen |
| 7,239,398 B2 | 7/2007 | De Groot et al. |
| 7,271,918 B2 | 9/2007 | De Groot et al. |
| 7,283,248 B2 | 10/2007 | Hill |
| 7,289,225 B2 | 10/2007 | De Groot |
| 7,298,494 B2 | 11/2007 | De Groot |
| 7,304,747 B2 | 12/2007 | De Lega |
| 7,315,382 B2 | 1/2008 | De Groot |
| 7,324,210 B2 | 1/2008 | De Groot et al. |
| 7,324,214 B2 | 1/2008 | De Groot et al. |
| 7,428,057 B2 | 9/2008 | De Lega et al. |
| 2001/0050773 A1 * | 12/2001 | De Groot et al. .......... 356/497 |
| 2002/0015146 A1 | 2/2002 | Meeks et al. |
| 2002/0135775 A1 | 9/2002 | de Groot et al. |
| 2002/0148955 A1 | 10/2002 | Hill |
| 2002/0196450 A1 | 12/2002 | Olszak et al. |
| 2003/0011784 A1 | 1/2003 | De Groot et al. |
| 2003/0048458 A1 | 3/2003 | Mieher et al. |
| 2003/0075721 A1 | 4/2003 | Li |

| | | |
|---|---|---|
| 2003/0112444 A1 | 6/2003 | Yang et al. |
| 2003/0137671 A1 | 7/2003 | De Groot et al. |
| 2003/0197871 A1 | 10/2003 | De Groot |
| 2004/0027576 A1 | 2/2004 | De Groot et al. |
| 2004/0075843 A1 | 4/2004 | Marron et al. |
| 2004/0085544 A1 | 5/2004 | De Groot et al. |
| 2004/0185582 A1 | 9/2004 | Kueny |
| 2004/0189999 A1 | 9/2004 | de Groot et al. |
| 2004/0233442 A1 | 11/2004 | Mieher et al. |
| 2004/0233444 A1 | 11/2004 | Mieher et al. |
| 2004/0246493 A1 | 12/2004 | Kim et al. |
| 2005/0024773 A1 | 2/2005 | Lillie |
| 2005/0029192 A1 | 2/2005 | Arnold et al. |
| 2005/0057757 A1 | 3/2005 | de Lega et al. |
| 2005/0068540 A1 | 3/2005 | de Groot et al. |
| 2005/0073692 A1 | 4/2005 | de Groot et al. |
| 2005/0078318 A1 | 4/2005 | de Groot |
| 2005/0078319 A1 | 4/2005 | de Groot |
| 2005/0088663 A1 | 4/2005 | de Groot et al. |
| 2005/0146727 A1 | 7/2005 | Hill |
| 2005/0179911 A1 | 8/2005 | Boomgarden et al. |
| 2005/0225769 A1 | 10/2005 | Bankhead et al. |
| 2005/0237534 A1 | 10/2005 | Deck |
| 2005/0237537 A1 | 10/2005 | Leizerson et al. |
| 2006/0012582 A1 | 1/2006 | de Lega |
| 2006/0072104 A1 | 4/2006 | Engel et al. |
| 2006/0119841 A1 | 6/2006 | Saunders et al. |
| 2006/0158657 A1 | 7/2006 | De Lega et al. |
| 2006/0158658 A1 | 7/2006 | Colonna De Lega et al. |
| 2006/0158659 A1 | 7/2006 | Colonna De Lega et al. |
| 2006/0170932 A1 | 8/2006 | Hayashi et al. |
| 2006/0187465 A1 | 8/2006 | De Groot |
| 2006/0262321 A1 | 11/2006 | De Groot |
| 2007/0008551 A1 | 1/2007 | Tang |
| 2007/0046953 A1 | 3/2007 | de Groot et al. |
| 2007/0081167 A1 | 4/2007 | De Groot et al. |
| 2007/0086013 A1 | 4/2007 | De Lega et al. |
| 2007/0091317 A1 | 4/2007 | Freischlad et al. |
| 2007/0091318 A1 | 4/2007 | Freishlad et al. |
| 2007/0091940 A1 | 4/2007 | Jameson |
| 2007/0097380 A1 | 5/2007 | De Groot et al. |
| 2007/0127036 A1 | 6/2007 | Liao et al. |
| 2007/0139656 A1 | 6/2007 | Wan |
| 2007/0247637 A1 | 10/2007 | De Groot |
| 2008/0018901 A1 | 1/2008 | de Groot |
| 2008/0088849 A1 | 4/2008 | de Lege et al. |

FOREIGN PATENT DOCUMENTS

| | | |
|---|---|---|
| DE | 4309056 | 9/1994 |
| EP | 0 397 388 A2 | 11/1990 |
| EP | 0 549 166 A2 | 6/1993 |
| EP | 0 617 255 A1 | 9/1994 |
| EP | 0 929 094 A2 | 7/1999 |
| GB | 2385417 | 8/2003 |
| JP | 8327327 | 12/1996 |
| JP | 09-218016 | 8/1997 |
| JP | 10-2855 | 1/1998 |
| JP | 10-325795 | 12/1998 |
| JP | 2000121317 | 4/2000 |
| JP | 2000-180124 | 6/2000 |
| JP | 2001-272603 | 10/2001 |
| JP | 2001-141652 | 5/2009 |
| KR | 20000061037 | 10/2000 |
| WO | WO 93/24805 | 12/1993 |
| WO | WO 94/00733 | 1/1994 |
| WO | WO 95/09343 | 4/1995 |
| WO | WO 97/44633 | 11/1997 |
| WO | WO 02/082008 | 10/2002 |
| WO | WO 03/036229 | 5/2003 |
| WO | WO 03/062802 | 7/2003 |
| WO | WO 2004/023071 | 3/2004 |
| WO | WO 2005/029192 | 3/2005 |

OTHER PUBLICATIONS

Abdulhalim, "Spectroscopic interference microscopy technique for measurement of layer parameters", Meas. Sci. Technol., vol. 12, pp. 1996-2001 (2001).

Akcay et al., "Spectral shaping to improve the point spread function in optical coherence tomography", Optics Letters, vol. 28, No. 20, pp. 1921-1923 (Oct. 15, 2003).

Azzam et al, "Ellipsometric function of a film-substrate system: Applications to the design of reflection-type optical devices and to ellipsometry", Journal of the Optical Society of America, vol. 5, No. 3, pp. 252-260 (1975).

Azzam et al., "Reflection and Transmission of Polarized Light by Stratified Planar Structures", Ellipsometry and Polarized Light, Elsevier Science B.V. ISBN 0 444 87016 4 (Paperback) pp. 267-363 (1987).

Bashkansky et al., "Signal Processing for Improving Field Cross-correlation Function in Optical Coherence Tomography", Supplement to Optics & Photonics News, 9(5) (May 1998).

Biegen, "Determination of the Phase Change on Reflection from Two-beam Interference," Optics Letters, 19:21:1690-1692, Nov. 1, 1994.

Bishop, et al., "Grating line shape characterization using scatterometry," SPIE 1545, 64-73 (1991).

Chim, S. S. C. and Kino, G. S., "Three-Dimensional Image Realization in Interference Microscopy", Applied Optics, May 10, 1992, vol. 31, No. 14.

Creath, "Step height measurement using two-wavelength phase-shifting interferometry", Applied Optics, vol. 26, No. 14, pp. 2810-2816 (Jul. 15, 1987).

Danielson et al., "Absolute Optical Ranging Using Low Coherence Interferometry," Applied Optics, 30:21:2975-2979, Jul. 20, 1991.

de Groot et al., "Angle-resolved three-dimensional analysis of surface films by coherence scanning interferometry", Optics Letters, vol. 32, No. 12, pp. 1638-1640 (Jun. 15, 2007).

de Groot et al.; "Three-dimensional imaging by sub-Nyquist sampling of white-light interfergrams"; Optics Letters vol. 18, No. 17; pp. 1462-1464, Sep. 1, 1993.

de Groot, "Extending the unambiguous range of two-color interferometers", Applied Optics, vol. 33, No. 25, pp. 5948-5953 (Sep. 1, 1994).

de Groot, "Three-color laser-diode interferometer", Applied Optics, vol. 30, No. 25, pp. 3612-3616 (Sep. 1, 1991).

de Groot, P., "Phase-shift calibration errors in interometers with spherical Fizeua cavities," Applied Optics, vol. 34:16, pp. 2856-2863 (Jun. 1, 1995).

de Lega, X., et al., "Optical topography measurement of patterned wafers," American Institute of Physics Conference Proceedings, vol. 788, pp. 432-436 (2005).

Debnath, S.K., et al., "Spectrally resolved phase-shifting interferometry of transparent thin films: sensitivity of thickness measurements," Appl. Opt. 45, 34 8636-8640 (2006).

Deck et al., "Two-color light-emitting-diode source for high-precision phase-shifting interferometry", Optics Letters, vol. 18, No. 22, pp. 1899-1901 (Nov. 15, 1993).

Encyclopedia of Laser Physics and Technology, http:\\www.rp-photonics.com\coherence.html, Mar. 14, 2008.

Encyclopedia of Laser Physics and Technology, http:\\www.rp-photonics.com\single mode fibers.html, Mar. 14, 2008.

Encyclopedia of Laser Physics and Technology, http:\\www.rp-photonics.com\photonic crystal fibers.html, Mar. 14, 2008.

Encyclopedia of Laser Physics and Technology, http:\\www.rp-photonics.com\supercontinuum generation.html, Mar. 14, 2008.

Gale et al., "Linnik microscope imaging of integrated circuit structures", Applied Optics vol. 35, No. 1, pp. 131-148 (Jan. 1, 1996).

Ghiglia et al., "Quality-Guided Path Following", Two-Dimensional Phase Unwrapping—Theory, Algorithms and Software, John Wiley & Sons publishers, ISBN 0-471-24935-1, pp. 122-136 (1998).

Hecht, "Basics of Coherence Theory," Optics, 2nd Ed., Addison Wesley, pp. 516-517 (1987).

Kleinknecht, et al., "Linewidth measurement on IC masks and wafers by grating test patterns," Appl. Opt. 19(4), 523-533 (1980).

Kohlhaas, A. Fromchen, C. and Brinkmeyer, E., "High-Resolution OCDR for Testing Integrated-Optical Waveguides: Dispersion-Corrupted Experimental Data Corrected by a Numerical Algorithm", Journal of Lightwave Technology, Nov. 1991, vol. 9, No. 11.

Naqvi, et al., "Linewidth measurement of gratings on photomasks: a simple technique," Appl. Opt., 31(10), 1377-1384 (1992).

Novak et al., "Template-based software for accurate MEMS characterization", Proceedings of SPIE, Fol. 4980, pp. 75-80 (2003).

Onodera et al., "Two-wavelength interferometry that uses a Fourier-transform method", Applied Optics, vol. 37, No. 34, pp. 7988-7994 (Dec. 1, 1998).

Peng, S.T., et al., "Theory of Periodic Dielect Waveguides," IEEE Trans Microwave Theory and Technique MTT-23(1), 123-133 (1975).

Pfortner et al., "Red-green-blue interferometer for the metrology of discontinuous structures", Applied Optics, vol. 42, No. 4, pp. 667-673 (Feb. 1, 2003).

Raymond, C.J., "Scatterometry for Semiconductor Metrology," in Handbook of silicon semiconductor metrology, A.J. Deibold, Ed. (Marcel Dekker, Inc., New York 2001).

Raymond, et al., "Scatterometry for CD measurements of etched structures," SPIE 2725, 720-728 (1996).

Schmit, J. et al., "Extended averaging technique for derivation of error-compensating algorithms in phase-shifting interferometry," Applied Optics, vol. 34:19, pp. 3610-3619 (Jul. 1, 1995).

Sheppard et al., "Effect of numerical aperture on interference fringe spacing", Applied Optics, vol. 34, No. 22, pp. 4731-4734 (Aug. 1, 1995).

Tzannes et al., Measurement of the modulation transfer function of infrared cameras, Optical Engineering, vol. 34, No. 6, pp. 1808-1817 (Jun. 1995). cited by other.

Wyant, "Phase shifting interferometry" (1998).

Youngquist, R. C. Carr, S. and Davies, D. E. N., "Optical Coherence-Domain Reflectometry: a New Optical Evaluation Technique", Optical Letters, Mar. 1987, vol. 12, No. 3.

Zhan, Q., et al., "Measurement of surface features beyond the diffraction limit with an imaging ellipsometer," Opt. Lett. 27, 821-823 (2002).

Berman et al., "Review of In Situ & In-line Detection for CMP Applications", Semiconductor Fabtech—$8^{th}$ Edition, pp. 267-274 (1998).

A. Bosseboeuf et al., "Application of microscopic interferometry techniques in the MEMS field", Proc. SPIE, 5145, pp. 1-16 (2003).

M. Davidson et al., "An Application of Interference Microscopy to Integrated Circuit Inspection and Metrology", Proceedings of SPIE, vol. 775, pp. 233-247 (1987).

Dresel, Thomas et al., "Three-dimensional sensing of rough surfaces by coherence radar", Applied Optics, vol. 31, No. 7, pp. 919-925 (Mar. 1, 1992).

Feke, Gilbert D. et al., "Interferometric back focal plane microellipsometry", Applied Optics, vol. 37, No. 10, pp. 1796-1802 (Apr. 1, 1998).

J.E. Greivenkamp, "Generalized data reduction for heterodyne interferometry", Opt. Eng., vol. 23 No. 4, pp. 350-352 (Jul./Aug. 1984).

P de Groot et al., "Signal modeling for low coherence height-scanning interference microscopy", Applied Optics, vol. 43 No. 25, pp. 4821-4830 (Sep. 1, 2004).

P. de Groot, "Derivation of algorithms for phase-shifting interferometry using the concept of a data-sampling window", Appl. Opt., 34(22), p. 4723-4730 (1995).

P. de Groot et al., "Signal modeling for modern interference microscopes", SPIE Proceedings, 5457-4 (2004).

Peter de Groot et al., "Determination of fringe order in white-light interference microscopy", Appl. Opt., 41(22) pp. 4571-4578 (2002).

P.A. Flournoy et al., "White-light interferometric thickness gauge", Appl. Opt., 11(9), pp. 1907-1915 (1972).

G. Hausler et al., "Coherence Radar and Spectral Radar—New Tools for Dermatological Diagnosis", Journal of Biomedical Optics, vol. 3, No. 1, pp. 21-31 (Jan. 1998).

R.D. Holmes et al., "Scanning microellipsometry for extraction of true topograpy", Electronics Letters, vol. 31, No. 5, pp. 358-359 (Mar. 2, 1995).

Seung-Woo Kim et al., "Thickness-profile measurement of transparent thin-film layers by white-light scanning interferometry", Applied Optics, vol. 38, No. 28, pp. 5968-5973 (Oct. 1, 1999).

Kieran G. Larkin, "Efficient nonlinear algorithm for envelope detection in white light interferometry", J. Opt. Soc. Am A4, pp. 832-843 (1996).

Kino, Gordon S. et al., "Mirau correlation microscope", Applied Optics, vol. 29, No. 26, pp. 3775-3783 (Sep. 10, 1990).

Kujawinska, Malgorzata, "Spatial Phase Measurement Methods", Interferogram Analysis: Digital Fringe Pattern Measurement Techniques, IOP Publishing Ltd. 1993, pp. 141-193.

Lee et al., "Profilometry with a coherence scanning microscope", Appl. Opt., 29(26), pp. 3784-3788 (1990).

I. Lee-Bennett, "Advances in non-contacting surface metrology", OF&T Workshop, paper OTuC1 (2004).

K. Leonhardt et al., "Micro-Ellipso-Height-Profilometry", Optics Communications, vol. 80, No. 3, 4, pp. 205-209 (Jan. 1, 1991).

Y. Liu et al., "Common path interferometric microellipsometry", SPIE, vol. 2782, pp. 635-645 (1996).

Lyakin et al., "The interferometric system with resolution better than coherence length for determination of geometrical thickness and refractive index of a layer object", Proceedings of the SPIE—The International Society for Optical Engineering SPIE-INT. Soc. Opt. Eng USA, vol. 4956, pp. 163-169 (Jul. 2003).

C.J. Morgan, "Least-Squares estimation in phase-measurement interferometry", Apt. Let., 7(8), pp. 368-370 (1982).

Ngoi et al., "Phase-shifting interferometry immune to vibration", Applied Optics, vol. 40, No. 19, pp. 3211-3214 (2001).

A.V. Oppenheim et al., "10.3: The time-dependent Fourier Transform", Discrete-Time Signal Processing, $2^{nd}$ Edition, pp. 714-722 (Prentice Hall, New Jersey, 1999).

M.C. Park et al., "Direct quadratic polynomial fitting for fringe peak detection of white light scanning interferograms", Opt. Eng, 39(4), pp. 952-959 (2000).

Pelligrand, S. et al., "Mesures 3D de topographies et de vibrations a l'echelle (sub)micrometrique par microscopie optique interferometrique", Proc. Club CMOI, Methodes et Techniques Optiques pour l'Industrie (2002).

Pluta, Maksymilian, "Advanced Light Microscopy", vol. 3, (Elsevier, Amsterdam, 1993) pp. 265-271.

W.H. Press et al., "Linear Correlation", Numerical Recipes in C, Cambridge University Press, $2^{nd}$ Edition, pp. 636-639 (1992).

Rosencwaig, Allan et al., "Beam profile reflectometry: A new technique for dielectric film measurements", Applied Physics Letters, vol. 60, No. 11, pp. 1301-1303 (Mar. 16, 1992).

Sandoz, Patrick "Wavelet transform as a processing tool in white-light interferometry", Optics Letters, vol. 22, No. 14, pp. 1065-1067 (Jul. 15, 1997).

P. Sandoz et al., "Optical implementation of frequency domain analysis for white light interferometry", Proceedings SPIE, vol. 2545,pp. 221-228 (Jun. 1995).

P. Sandoz et al., "High-resolution profilometry by using phase calculation algorithms for spectroscopic analysis of white-light interferograms", Journal of Modem Optics, vol. 43, No. 4, pp. 701-708 (1996).

P. Sandoz et al., "Processing of white light correlograms: simultaneous phase and envelope measurements by wavelet transformation", SPIE, 3098, pp. 73-82 (1997).

U. Schnell et al., "Dispersive white-light interferometry for absolute distance measurement with dielectric multilayer systems on the target", Optics Letters, vol. 21, No. 7, pp. 528-530 (Apr. 1996).

J. Schwider et al., "Dispersive interferometric profilometer", Optics Letters, vol. 19, No. 13, pp. 995-997 (Jul. 1994).

C.W. See et al., "Scanning optical microellipsometer for pure surface profiling", Applied Optics, vol. 35, No. 34, pp. 6663-6668 (Dec. 1, 1996).

Shatalin, S.V. et al., "Reflection conoscopy and micro-ellipsometry of isotropic thin film structures", *Journal of Microscopy*, vol. 179, Part 3, pp. 241-252 (Sep. 1995).

M. Totzeck, "Numerical simulation of high-NA quantitative polarization microscopy and corresponding near-fields", *Optik*, vol. 112, No. 9, pp. 399-406 (2001).

R. Tripathi et al., "Spectral shaping for non-Gaussian source spectra in optical coherence tomography", *Optics Letters*, vol. 27, No. 6, pp. 406-408 (2002).

D. Willenborg et al, "A novel micro-spot dielectric film thickness measurement system", *SPIE*, vol. 1594, pp. 322-333 (1991).

* cited by examiner

INTERFEROMETRY METHOD FOR ELLIPSOMETRY, REFLECTOMETRY, AND SCATTEROMETRY MEASUREMENTS, INCLUDING CHARACTERIZATION OF THIN FILM STRUCTURES

CROSS-REFERENCE TO RELATED APPLICATIONS

This application is a continuation of prior U.S. patent application Ser. No. 11/760,163, filed Jun. 8, 2007, now U.S. Pat. No. 7,403,289, which is a continuation of prior U.S. patent application Ser. No. 11/542,617, filed Oct. 3, 2006, now U.S. Pat. No. 7,315,382, which is a continuation of prior U.S. patent application Ser. No. 10/659,060, filed Sep. 9, 2003, now U.S. Pat. No. 7,139,081, which, in turn, claims priority to each of: U.S. Provisional Patent Application Ser. No. 60/409,147 filed Sep. 9, 2002 and entitled "Back-Focal Plane Ellipsometry, Reflectometry and Scatterometry By Fourier Analysis Of Vertically-Scanned Interference Data;" U.S. Provisional Patent Application Ser. No. 60/452,615 filed Mar. 6, 2003 and entitled "Profiling Complex Surface Structures Using Height Scanning Interferometry;" and U.S. Provisional Patent Application Ser. No. 60/478,300 filed Jun. 13, 2003 and entitled "Scanning Interferometry." The contents of the prior applications are incorporated herein by reference in their entirety.

BACKGROUND

The invention relates to surface topography measurements of objects having thin films or discrete structures of dissimilar materials. Such measurements are relevant to the characterization of flat panel display components, semiconductor wafer metrology, and in-situ thin film and dissimilar materials analysis.

Ellipsometry can be used to analyze the optical properties of a complex surface. Ellipsometry relies on the difference in complex reflectivity of a surface when illuminated at an oblique angle, e.g. 60°, sometimes with a variable angle or with multiple wavelengths. Many types of ellipsometer are known in the art.

To achieve greater resolution than is readily achievable in a conventional ellipsometer, microellipsometers measure phase and/or intensity distributions in the back focal plane of the objective, also known as the pupil plane, where the various illumination angles are mapped into field positions. Such devices are modernizations of traditional polarization microscopes or "conoscopes," linked historically to crystallography and mineralogy, which employs crossed polarizers and a Bertrand lens to analyze the pupil plane birefringent materials.

SUMMARY

Embodiments of the invention are based, at least in part, on the realization that the various angles of incidence in an interferometer (e.g., having a high NA objective) can be distinguished by the corresponding spatial frequencies in an interference pattern generated by scanning the test sample or reference mirror relative to the interferometer (e.g., towards or away from the objective used to focus light onto the test sample or reference mirror). Therefore, a mathematical spatial frequency decomposition of such an interference pattern provides access to the relative amplitude and phase of the light reflected (or scattered) from a sample surface as a function of angle. This knowledge, together with a calibration of the illumination distribution in the pupil of the objective and the polarization state of the illumination across the pupil plane, provides the multiple-angle reflection (or scattering) amplitude and phase information for every pixel in the field of view, without having to directly image the pupil plane onto a detector array. These multiple-angle data can be used to provide sample surface characteristics such as thin film thickness and/or the complex index of refraction on a pixel-by-pixel basis with high lateral resolution, simultaneously with surface height profile information.

Embodiments of the invention typically include an interferometer, for example an interference microscope having an interference objective of the Mirau, Linnik, Michelson type or the like. The objective illuminates and collects light from a sample surface over a range of incident angles $\phi$. For example, $\phi=0$ to $50°$ for an interference objective having a numerical aperture (NA) of about 0.75. The polarization of the illumination may be radial, linear, circular, field-dependent, or adjustable. Typically, the apparatus further includes a mechanical scanner for displacing the sample surface along an axis parallel to the optical axis of the objective (or equivalent motion objective with respect to the sample) while an electronic camera collects interference intensity data for an array of pixels corresponding to field positions on the sample. Alternatively, a reference leg of the interferometer may be scanned. The result is intensity vs. sample position data for each pixel for a sequence of objective distances from the sample, stored in computer memory.

In some embodiments, the computer transforms the interference data for each pixel into the frequency domain e.g. by Fourier analysis, to recover the magnitude and phase of the constituent spatial frequencies present in the interference data. The computer analyzes these data, compares the magnitude and phase to a model representing the surface structure of the sample, including incident-angle, polarization and/or wavelength-dependent optical properties of the sample. This analysis determines parameters such as surface height and thin film thickness.

Some embodiments select wavelengths or send multiple wavelengths into the interferometer to perform a detailed analysis of the optical properties of materials as function of wavelength, in addition to analyzing their angle-dependence. Some embodiments analyze the scattered light from the sample to determine surface structure information by the diffractive and scattering properties of the surface as a function of incident angle and wavelength.

Embodiments of the invention include many advantages. For example, embodiments may provide a means for analyzing a surface structure for its optical properties and surface topography simultaneously, e.g., on a pixel-by-pixel basis, by frequency-domain decomposition of interference patterns generated by vertical scanning of the sample with respect to the interference objective. Such an approach provides access to the angle-dependent and wavelength-dependent optical properties of the surface, using both amplitude and phase information from the reflected light without the need to directly access the pupil plane of the instrument.

We now generally summarize different aspects and features of one or more embodiments of the invention.

In general, in one aspect, the invention features a method including: imaging test light emerging from a test object over a range of angles to interfere with reference light on a detector, wherein the test and reference light are derived from a common source; for each of the angles, simultaneously varying an optical path length difference from the source to the detector between interfering portions of the test and reference light at a rate that depends on the angle at which the test light emerges from the test object; and determining an angle-dependence of an optical property of the test object based on the interference between the test and reference light as the optical path length difference is varied for each of the angles.

Embodiments of the method may include any of the following features.

The range of incident angles may correspond to a numerical aperture greater than 0.7, or more preferably, greater than 0.9.

The detector may be a camera having multiple detector elements and the imaging may include imaging the test light emerging from different locations of the test object to corresponding locations on the camera. Furthermore, determining the angle-dependence of the optical property may include determining the angle-dependence of the optical property at each of the different locations of the test object.

The angle-dependence of the optical property may relate to changes in the optical property as a function of angle of the test light incident on the test object. The method may further include illuminating multiple locations of the test object with the test light such that the test light is incident on each of the multiple locations over the range of incident angles. In such cases, the illuminating and the imaging may involve a common objective lens. Furthermore, the common source may be a spatially extended source.

In other embodiments, the angle-dependence of the optical property relate to changes in the optical property as a function of angle of the test light scattered (or diffracted) from the test object. The method may further include illuminating multiple locations of the test object with the test light having a uniform angle of incidence on the test object, and wherein the imaging may include imaging test light scattered over a range of angles from each location of the test object to a corresponding location on the detector. In such cases, the illuminating and the imaging may involve a common objective lens. Furthermore, the common source may be a point source.

The imaging may further include polarizing the test light in a pupil plane of an optical system involved in the imaging.

The method may further include illuminating the test object with the test light and polarizing the test light in a pupil plane of an optical system used to illuminate the test object.

The common source may be monochromatic. For example, the common source may have a central wavelength and a spectral bandwidth less than 2% of the central wavelength.

The simultaneous varying of the optical path length difference for each of the angles may include moving the test object relative to an objective used to collect the test light emerging from the test sample.

The simultaneous varying of the optical path length difference for each of the angles may include moving a reference mirror used to reflect the reference light relative to an objective used to focus the reference light onto the reference mirror.

The simultaneous varying of the optical path length difference for each of the angles may include moving a beam splitter positioned within a Mirau interference objective.

The simultaneous varying of the optical path length difference for each of the angles may define a spatial coherence length, and the optical path length difference for at least one of the angles may be varied over a range larger than the spatial coherence length.

Determining the angle-dependence of the optical property may include: measuring an interference signal from the detector as the optical path length difference is simultaneously varied for each of the angles; and transforming the interference signal with respect to a coordinate linearly proportional the optical path length difference for each of the angles to produce a transformed signal that depends on a conjugate variable to the coordinate. For example, the conjugate variable may spatial frequency.

The conjugate variable may provide a direct mapping to the angle of test light incident on, or emerging from, the test object. For example, when the conjugate variable is spatial frequency K, the direct mapping between the spatial frequency and the angle $\phi$ may be given by $K(\phi) \propto \cos(\phi)/\lambda$, where $\lambda$ is the wavelength of the test light. For example, when the emerging light is reflected from the test sample, the direct mapping between the spatial frequency and the angle may be given by $K(\phi)=4\pi \cos(\phi)/\lambda$.

The transformed signal may provide a direct mapping to the angle-dependence of the optical property. For example, the transformation may correspond to a Fourier transform.

The optical property may be related to the complex reflectivity of the test object. For example, the optical property may be related to the magnitude of the complex reflectivity of the test object. Also, the optical property may be related to the phase of the complex reflectivity of the test object.

The angle-dependence of the optical property may be determined based on the interference between the test and reference light as the optical path length difference is varied for each of the angles and precalibrated angle-dependent characteristics of an optical system involved in the imaging.

The method may further include determining a surface height profile of the test object based on the interference between the test and reference light as the optical path length difference is varied.

The method may further including comparing the angle-dependent changes in the optical property determined from the interference between the test and reference light to those of a model for the test object. For example, the test object may include at least one thin film on a substrate, and the method may further include determining a thickness of the thin film based on the comparison.

In one such embodiment, the optical property includes the magnitude of the angle-dependence of the complex reflectivity of the test sample, and the determination of the thickness of the thin film is based on comparing the magnitude of the angle-dependence of the complex reflectivity to that of the model. Furthemore, the embodiment may include determining a surface height profile for the test object based on the comparison. For example, the optical property may further include the phase of the angle-dependence of the complex reflectivity of the test sample, and the determination of the surface height profile is based on the determined thickness of the thin film and comparing the phase of the angle-dependence of the complex reflectivity to that of the model for the determined thickness.

Finally, the test and reference light may have a first wavelength, and the method may further include repeating the imaging, varying, and determining for test and reference light having a second wavelength different from the first wavelength.

In general, in another aspect, the invention features a method including: determining an angle-dependence of an optical property of a test object based on scanning interferometry data for the test object.

This method may further include any of the features described above in connection with the first method.

In general, in yet another aspect, the invention features a method including: imaging test light emerging from a test object over a range of angles to interfere with reference light on a detector, wherein the test and reference light are derived from a monochromatic, common source and wherein the test object includes at least one thin film on a substrate; for each of the angles, simultaneously varying an optical path length difference from the source to the detector between interfering portions of the test and reference light at a rate that depends on the angle at which the test light emerges from the test object; and determining a thickness of the thin film based on the interference between the test and reference light as the optical path length difference is varied for each of the angles.

In general, in yet another aspect, the invention features a method including: determining a thickness of a thin film on a test object including the thin film and a substrate supporting the thin film based on monochromatic scanning interferometry data for the test object.

Embodiments of the third and fourth methods described above may further include any of the features described above in connection with the first method.

In general, in yet another aspect, the invention features an apparatus including: a light source; a detector; a scanning interferometer configured to image test light emerging from a test object over a range of angles to interfere with reference light on the detector, wherein the test and reference light are derived from the light source, wherein for each of the angles, the scanning interferometer is further configured to simultaneously vary an optical path length difference from the source to the detector between interfering portions of the test and reference light at a rate that depends on the angle at which the test light emerges from the test object; and an electronic processor coupled to the detector and the scanning interferometer, wherein the electronic processor is configured to determine an angle-dependence of an optical property of the test object based on the interference between the test and reference light as the optical path length difference is varied for each of the angles as measured by the detector.

In general, in yet another aspect, the invention features an apparatus including: a monochromatic light source; a detector; a scanning interferometer configured to image test light emerging from a test object over a range of angles to interfere with reference light on the detector, wherein the test and reference light are derived from the monochromatic light source, wherein for each of the angles, the scanning interferometer is further configured to simultaneously vary an optical path length difference from the source to the detector between interfering portions of the test and reference light at a rate that depends on the angle at which the test light emerges from the test object; and an electronic processor coupled to the detector and the scanning interferometer, wherein the electronic processor is configured to determine a thickness of a thin film on the test object based on the interference between the test and reference light as the optical path length difference is varied for each of the angles.

In general, in yet another aspect, the invention features an apparatus including: a scanning interferometry system; and an electronic processor coupled to the scanning interferometry system, wherein the electronic processor is configured to determine an angle-dependence of an optical property of a test object based on scanning interferometry data for the test object produced by the scanning interferometry system.

In general, in yet another aspect, the invention features an apparatus including: a monochromatic scanning interferometry system; and an electronic processor coupled to the scanning interferometry system, wherein the electronic processor is configured to determine a thickness of a thin film on the test object based on monochromatic scanning interferometry data for the test object.

In general, in yet another aspect, the invention features an apparatus including: a scanning interferometer configured to image test light emerging from a test object over a range of angles to interfere with reference light on a detector, wherein the test and reference light are derived from a common source, wherein for each of the angles, the scanning interferometer is further configured to simultaneously vary an optical path length difference from the source to the detector between interfering portions of the test and reference light at a rate that depends on the angle at which the test light emerges from the test object, wherein the interferometer includes an objective lens positioned to collect the test light emerging from the test object and at least one polarization optic positioned in a pupil plane of the objective.

For example, the at least one polarization optic may impart a polarization that varies across the pupil plane.

Also, the at least one polarization optic may include a polarizer and at least one waveplate. For example, the at least one polarization optic may include two waveplates located a different positions in the pupil plane.

In general, in yet another aspect, the invention features an apparatus including: a scanning interferometer configured to image test light emerging from a test object over a range of angles to interfere with reference light on a detector, wherein the test and reference light are derived from a common source, wherein for each of the angles, the scanning interferometer is further configured to simultaneously vary an optical path length difference from the source to the detector between interfering portions of the test and reference light at a rate that depends on the angle at which the test light emerges from the test object, wherein the interferometer comprises a source module configured to illuminate the test object with substantially collimated light. For example, the apparatus may further include the common source, and the common source may be a monochromatic source.

Furthermore, embodiments of any of the preceding apparatus inventions may include any of the corresponding features described above in connection with the first method. Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control.

Other features, objects, and advantages of the invention will be apparent from the following detailed description.

BRIEF DESCRIPTION OF THE DRAWINGS

Like reference numerals in different drawings refer to common elements.

DETAILED DESCRIPTION

Figure 1:
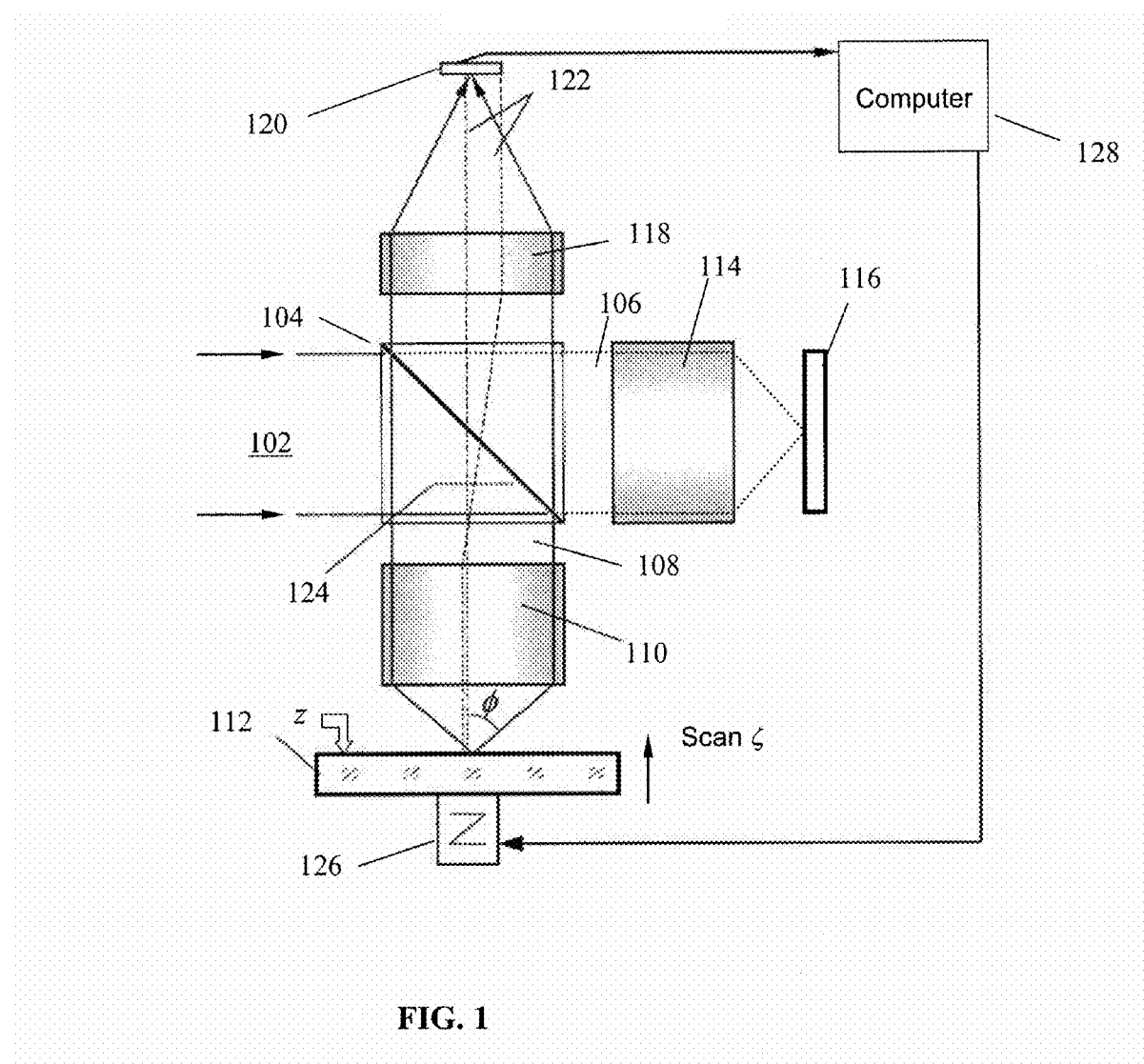
FIG. 1 is a schematic drawing of a Linnik-type, scanning interferometry system.

FIG. 1 shows a scanning interferometer of the Linnik type. Illumination light 102 from a source (not shown) is partially transmitted by a beam splitter 104 to define reference light 106 and partially reflected by beam splitter 104 to define measurement light 108. The measurement light is focused by a measurement objective 110 onto a test sample 112 (e.g., a sample comprising a thin single- or multi-layer film of one or more dissimilar materials). Similarly, the reference light is focused by a reference objective 114 onto a reference mirror 116. Preferably, the measurement and reference objectives have common optical properties (e.g., matched numerical apertures). Measurement light reflected (or scattered or diffracted) from the test sample 112 propagates back through measurement objective 110, is transmitted by beam splitter 104, and imaged by imaging lens 118 onto a detector 120. Similarly, reference light reflected from reference mirror 116 propagates back through reference objective 114, is reflected by beam splitter 104, and imaged by imaging lens 118 onto a detector 120, where it interferes with the measurement light.

For simplicity, FIG. 1 shows the measurement and reference light focusing onto particular points on the test sample and reference mirror, respectively, and subsequently interfering on a corresponding point on the detector. Such light corresponds to those portions of the illumination light that propagate perpendicular to the pupil planes for the measurement and reference legs of the interferometer. Other portions of the illumination light ultimately illuminate other points on the test sample and reference mirror, which are then imaged onto corresponding points on the detector. In FIG. 1, this is illustrated by the dashed lines 122, which correspond to the chief rays emerging from different points on the test sample that are imaged to corresponding points on the detector. The chief rays intersect in the center of the pupil plane 124 of the measurement leg, which is the back focal plane of measurement objective 110. Light emerging from the test sample at an angle different from that of the chief rays intersect at a different location of pupil plane 124.

In preferred embodiments, detector 120 is a multiple element (i.e., multi-pixel) camera to independently measure the interference between the measurement and reference light corresponding to different points on the test sample and reference mirror (i.e., to provide spatial resolution for the interference pattern).

A scanning stage 126 coupled to test sample 112 scans the position of the test sample relative to measurement objective 110, as denoted by the scan coordinate $\zeta$ in FIG. 1. For example, the scanning stage can be based on a piezoelectric transducer (PZT). Detector 120 measures the intensity of the optical interference at one or more pixels of the detector as the relative position of the test sample is being scanned and sends that information to a computer 128 for analysis.

Because the scanning occurs in a region where the measurement light is being focused onto the test sample, the scan varies the optical path length of the measurement light from the source to the detector differently depending on the angle of the measurement light incident on, and emerging from, the test sample. As a result, the optical path difference (OPD) from the source to the detector between interfering portions of the measurement and reference light scale differently with the scan coordinate $\zeta$ depending on the angle of the measurement light incident on, and emerging from, the test sample. In other embodiments of the invention, the same result can be achieved by scanning the position of reference mirror 116 relative to reference objective 114 (instead of scanning test sample 112 relative to measurement objective 110).

This difference in how OPD varies with the scan coordinate $\zeta$ introduces a limited coherence length in the interference signal measured at each pixel of the detector. For example, the interference signal (as a function of scan coordinate) is typically modulated by an envelope having a spatial coherence length on the order of $\lambda/2(NA)^2$, where $\lambda$ is the nominal wavelength of the illumination light and NA is the numerical aperture of the measurement and reference objectives. As described further below, the modulation of the interference signal provides angle-dependent information about the reflectivity of the test sample. To increase the limited spatial coherence, the objectives in the scanning interferometer preferably define a large numerical aperture, e.g., greater than 0.7 (or more preferably, greater than 0.9).

The interference signal can be further modulated by a limited temporal coherence length associated with the spectral bandwidth of the illumination source. For the present description, however, it is assumed that the illumination source is nominally monochromatic and any limitation in temporal coherence is small relative to the limited spatial coherence. For example, the illumination source may have bandwidth that is less than about 2% of its central wavelength.

Referring again to the Linnik interferometer of FIG. 1, measurement objective 110 illuminates and views the surface of the test sample over a range of incident angles $\phi$. The interference effect will now be calculated mathematically using a simplified model, assuming monochromatic illumination. Thereafter, it will be explained how the optical properties of the sample surface are recovered by mathematical decomposition of the interference pattern into its angle-dependent contributions.

The complex amplitude reflectivity of the surface of the test sample is $z(\phi)$ and the corresponding intensity reflectivity $Z(\phi)$ is $$Z(\phi)=|z(\phi)|^2. \qquad (1)$$

The phase change on reflection (PCOR) for the sample surface is $$\alpha z(\phi)=\arg[z(\phi)] \qquad (2),$$

where "arg" in Eq. (2) returns the phase of the complex amplitude reflectivity.

In a simplified scalar (non-polarized) model in which one considers the interference effects for each angle of incidence separately, the interference pattern for a single sample point or camera pixel is proportional to $$g(\phi,\zeta,h) = R_0(\phi) + Z(\phi) + V_0(\phi)\sqrt{Z(\phi)}\cos[(h-\zeta)K(\phi) + \alpha_0(\phi) + \alpha_z(\phi)] \quad (3)$$

where $\zeta$ is the scan position (actuated by the PZT) and h is the height profile of the sample surface. The parameters $R_0(\phi)$, $V_0(\phi)$ and $\alpha_0(\phi)$ are DC level, contrast and phase values characteristic of the interferometer optics, including reference mirror 116, that are independent of test sample 112. As described further below, a calibration procedure determines these parameters using a known artifact of known optical characteristics. The $R_0(\phi)$, $V_0(\phi)$ and $\alpha_0(\phi)$ parameters may include a field dependence, as required, to accommodate the optical properties of the instrument.

The spatial frequency $K(\phi)$ of the interference effect decreases as a function of angle $\phi$ according to $$K(\phi) = \frac{4\pi}{\lambda}\cos(\phi), \quad (4)$$

where $\lambda$ is the illumination wavelength, and it is assumed that the measurement light is reflected from the test sample (i.e., measurement light emerges from the test sample at an angle equal to that at which it was incident on the test sample). Eq. (4) is based on the fact that the scanning is done where the measurement light (or reference light) propagates over a range of angles, and thus the OPD between interfering portions of the measurement and reference light scale differently with the scan coordinate $\zeta$ depending on the angle of the measurement light incident on the test sample. As a result, Eq. (4) sets forth a unique relationship between the spatial frequency in the interference signal and angle of incidence.

Figure 2:
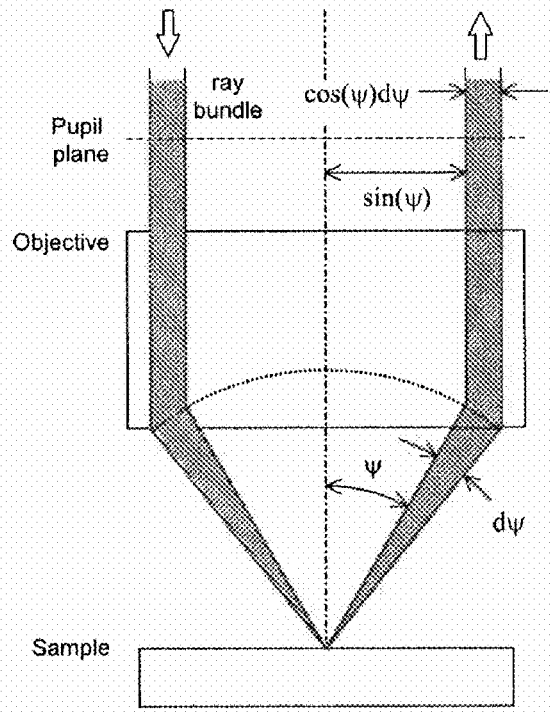
FIG. 2 is a diagram showing illumination of the test sample through an objective lens.

Assuming the source light is perfectly incoherent spatially across the pupil and is monochromatic, the net effect of all of the angle-dependent contributions to the interference phenomenon is given by the incoherent superposition integral $$I(\zeta,h) = \int_0^{\phi_{MAX}} g(\phi,\zeta,h)P(\phi)d\phi \quad (5)$$

where $\phi_{MAX} = \arcsin(NA)$ and the weighting function $$P_\phi = \sin(\phi)\cos(\phi) \quad (6)$$

used in the examples that follow is appropriate for a pupil uniformly illuminated with light, which is apparent from the consideration of the diagram in FIG. 2 (in which the angle is denoted by $\psi$ rather than $\phi$).

For each pixel, the electronic camera and computer control measure the interference pattern $I(\zeta,h)$ over a range of scan positions $\zeta$. The height h and the effective reflectivity $z(\phi)$ vary across the field and may be different for each pixel.

The unique relationship between spatial frequency and angle of incidence provides a means of recovering the individual contributions $g(\phi,\zeta,h)$ to the integrated pattern $I(\zeta,h)$. The first step is to perform a decomposition of the complete interference pattern, for example, by Fourier transformation:

$$q[K(\phi),h] = \int_{-\infty}^{\infty} I(\zeta,h)\exp[iK(\phi)\zeta]d\zeta. \quad (7)$$

The practical requirement of a limited scan truncates the integration over all $\zeta$ in Eq. (7) to a limited range of values that include as much of the interference signal as required for accurate results. Any other transform that similarly decomposes the interference pattern may also be used. The transform into a spatial frequency domain is generally referred to as frequency domain analysis (FDA).

The decomposition $q[K(\phi),h]$ may be interpreted as follows. The zero spatial frequency or DC terms are not separable as a function of angle $\phi$, therefore $$q(0,h) = \int_0^{\phi_{MAX}} P(\phi)[R_0(\phi) + Z(\phi)]d\phi. \quad (8)$$

For all other spatial frequency components having a spatial period much smaller than the actual can range in the integration, the magnitude of $q[K(\phi),h]$ is $$Q(\phi,h) = |q[K(\phi),h]| = P(\phi)V_0(\phi)\sqrt{Z(\phi)} \quad (9)$$

and the complex phase is $$\alpha_Q(\phi,h) = \arg\{q[K(\phi),h]\} = hK(\phi) + \alpha_0(\phi) + \alpha_z(\phi). \quad (10)$$

In one embodiment of the invention, the optical system characteristics $\alpha_0(\phi)$, $P(\phi)$, $V_0(\phi)$ have been determined by prior calibration, e.g., by means of a known artifact sample, as was noted in the text accompanying Eq. (3). For example, the measurement can be made with a test sample having a known surface height and reflectivity so that the optical system characteristics can be extracted from the Eqs. (9) and (10). With the optical system characteristics having been predetermined, Eqs. (9) and (10) provide information on the surface height h and the two optical properties $Z(\phi)$ and $\alpha_z(\phi)$ of the surface over the range of incident angles $\phi$. The optical properties $Z(\phi)$ and $\alpha_z(\phi)$ are themselves often linked by fundamental principles, such as the known optical properties of materials and thin films, to specific surface parameters such as film thickness. Thus these parameters together with the surface height can be adjusted so as to provide the best fit to the measure phase $\alpha_Q(\phi,h)$ and magnitude $Q(\phi,h)$ of $q[K(\phi),h]$.

Figure 3:
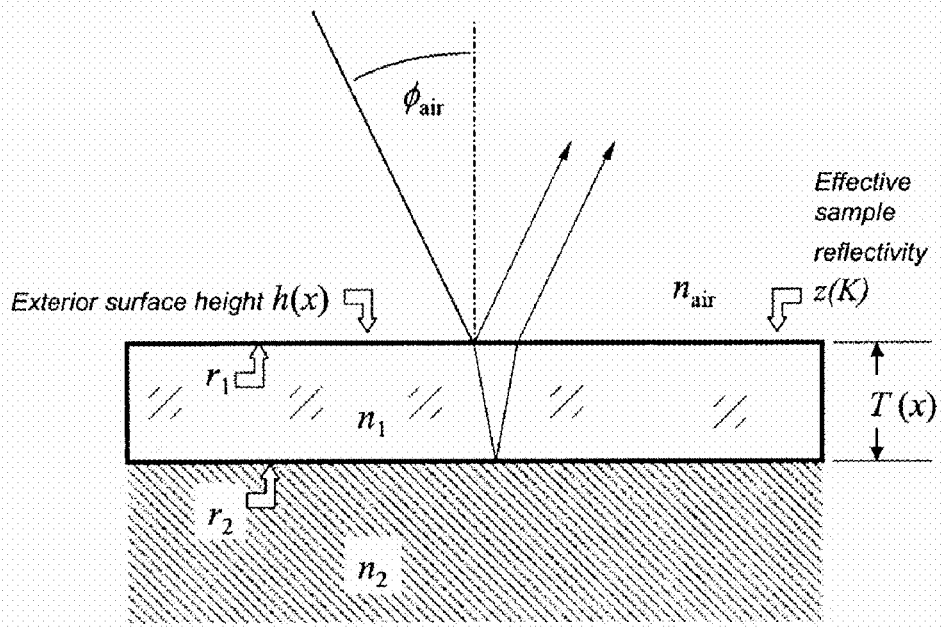
FIG. 3 is a diagram of a thin film structure.

As an example, consider the thin-film structure of FIG. 3. The effective reflectivity of this structure is given by $$z(\phi) = \frac{r_1(\phi) + r_2(\phi')\exp[iK(\phi')T]}{1 + r_1(\phi)r_2(\phi')\exp[iK(\phi')T]} \quad (11)$$

where $r_1(\phi), r_2(\phi')$ are the reflectivities of the upper and lower surfaces, respectively, and $\phi'$ is the angle of incidence on the lower surface calculated from $\phi$ and Snell's law. The thin-film Eq. (11) generates distinctive interference effects with a strong dependence on $K(\phi)$.

For a quantitative illustration of this example, consider a 1.8-micron film of silicon dioxide ($SiO_2$; index $n_1 = 1.46$) on silicon (Si; index $n_2 = 3.96 + 0.03i$) and an illumination wavelength of 550 nm. The effective reflectivity $z(\phi)$ follows from Eq. (11) and the Fresnel equations for the reflectivities of the interfaces. A scan of this sample surface with respect to the interference objective generates an signal such as in FIG. 4. For comparison, FIG. 5 shows a simulated, interference pattern $I(\zeta,h)$ for a simple single-surface $SiO_2$ sample (i.e., a thick sample of $SiO_2$ with no thin film layer).

Figure 4:
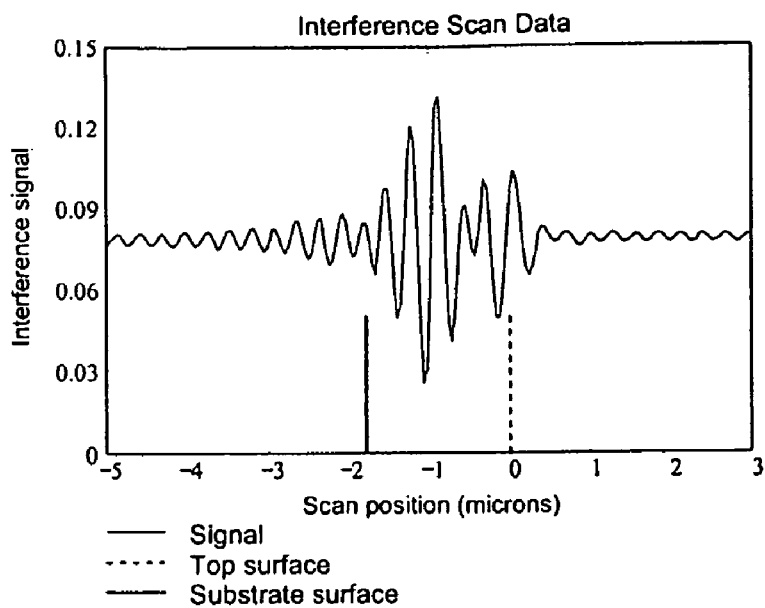
FIG. 4 is a simulated interference pattern $I(\zeta,h)$ for the structure shown in FIG. 3 built up of 1.8-μm of $SiO_2$ on Si, using 550-nm monochromatic light and a 0.9-NA Linnik objective. Note that the interference signals from both surfaces are mixed together.
Figure 5:
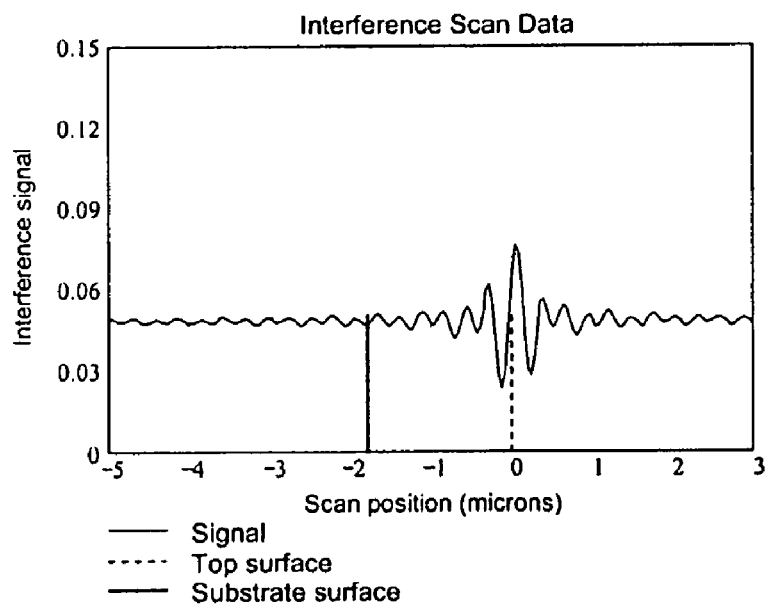
FIG. 5 is a simulated interference pattern $I(\zeta,h)$ for a simple single-surface $SiO_2$ sample (i.e., no thin films), for comparison with FIG. 4.
Figure 6:
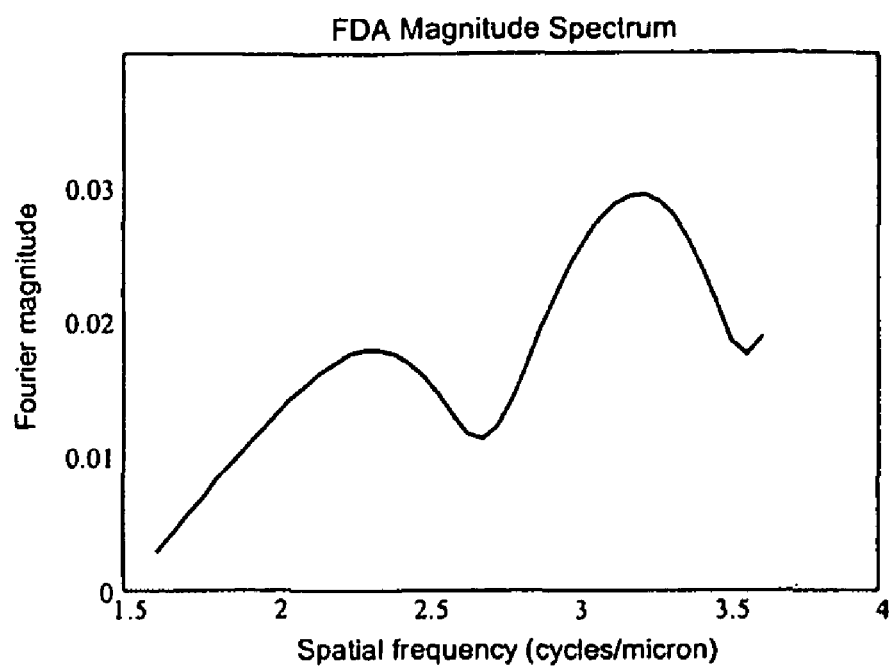
FIG. 6 is a graph showing the magnitude Q ($\phi$, h) of the Fourier transform of the signal in FIG. 4 generated by vertically scanning the thin-film structure of FIG. 3. The spatial frequency relates to incident angle according to Eq. (4).

After data acquisition, the computer transforms signals similar to that of FIG. 4 for each image pixel into the frequency domain. The signals and transforms may differ from pixel to pixel because of field variations in surface topography, optical system parameters, and film thickness. FIG. 6 shows the magnitude (in this case, the amplitude) of each of the constituent spatial frequency contributions to the signal in FIG. 4. This result shows very distinctive features when compared to the frequency-domain magnitude shown in FIG. 7 generated by a simple single-surface structure having the interference signal shown in FIG. 5.

Figure 7:
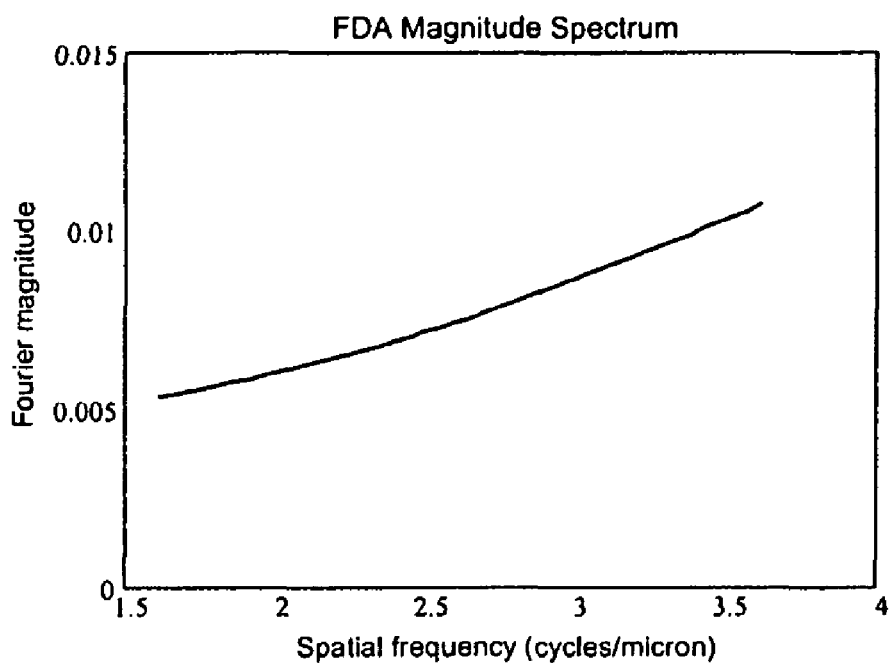
FIG. 7 is a graph showing the magnitude $Q(\phi,h)$ of the Fourier transform of the signal in FIG. 5 for the single-surface sample. The increasing magnitude at lower spatial frequencies is the result of increasing reflectivity at shallow angles of incidence.
Figure 8:
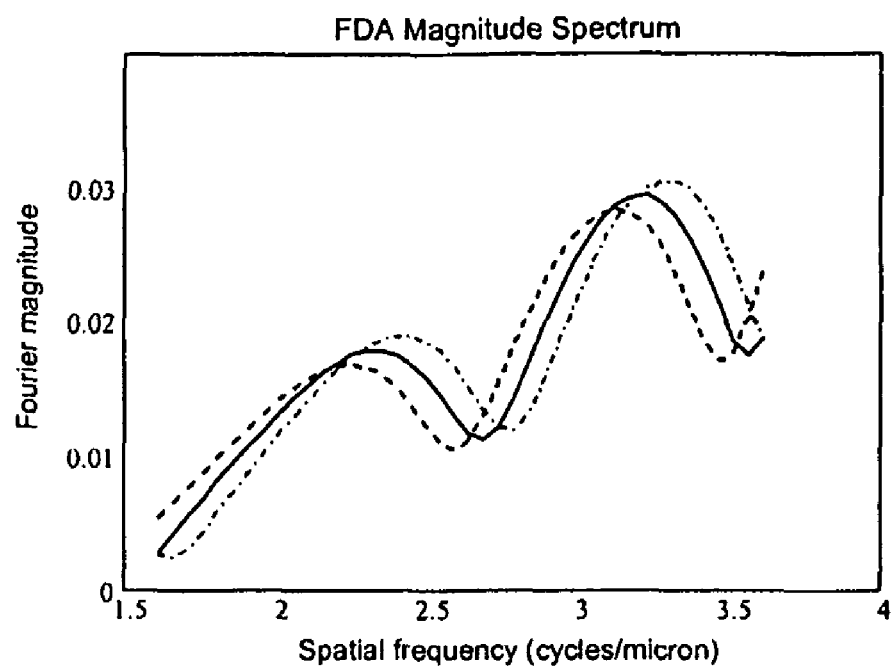
FIG. 8 is a graph comparing the expected result of $P(\phi)V_0(\phi)\sqrt{Z(\phi)}$ for the $SiO_2$ on Si thin film structure of FIG. 3 for three film thicknesses in 0.02-μm increments (see Eq. (9)).

Comparison of FIG. 6 with FIG. 7, for example using FIG. 7 as a calibration, provides an unambiguous determination of the presence of a thin film. Further, by comparing FIG. 6 with the theoretical expectation based on the effective reflectivity of the sample, the computer can determine, e.g., the thickness of the film assuming the known properties of $SiO_2$ and Si. This is illustrated by FIG. 8, which compares the expected results of three different films, only one of which (1.80 μm) provides a good match to the Fourier Transformed interference data of FIG. 6.

Figure 9:
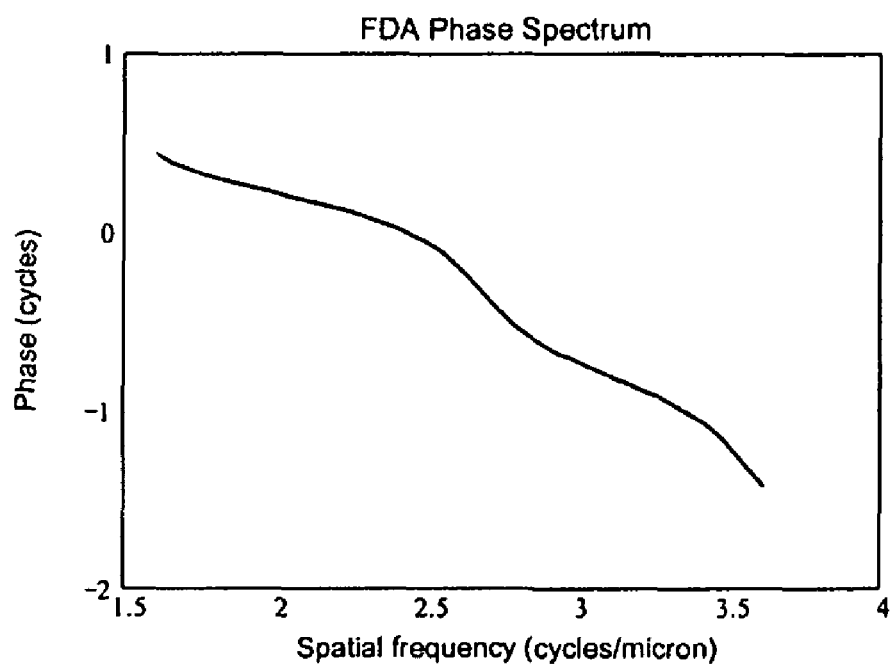
FIG. 9 is a graph of the phase $\alpha_O(\phi,h)$ as a function of spatial frequency for the signal in FIG. 4 generated by vertically scanning the thin-film structure of FIG. 3. The spatial frequency relates to incident angle according to Eq. (4). Note not only the slope of the phase but the distinctive nonlinearity compared to the simpler single-surface reflection in FIG. 10.
Figure 10:
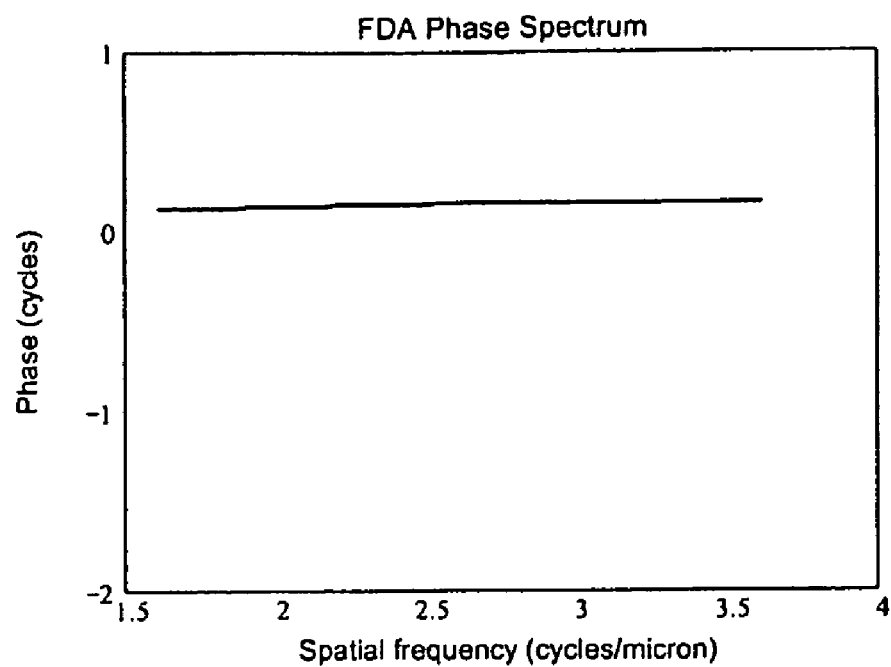
FIG. 10 is a graph of the phase $\alpha_O(\phi,h)$ as a function of spatial frequency for the signal in FIG. 5 for the single-surface pattern, for comparison with FIG. 9.

A similar analysis is also useful for the phase of the Fourier Transform. FIG. 9 and FIG. 10 show the difference between a thin-film structure and a simple homogeneous, single-surface sample. The nonlinearity evident in FIG. 9 is a clear signature of a thin film effect. Here again, comparison between measurement and theory provides important film thickness information, based on Eq. (10). Furthermore, using the thickness information derived from the amplitude information, one can determine $\alpha_z(\phi)$ from Eq. (11) and use it in Eq. (10) to extract the surface height variation h among the different pixels.

In other embodiments, an interferometry system different from that in FIG. 1 may be used to provide the scanning interferometry data I(ζ,h) at each pixel of the camera. For example, the interferometry system may be a Mirau-type interferometer as shown in FIG. 11.

Figure 11:
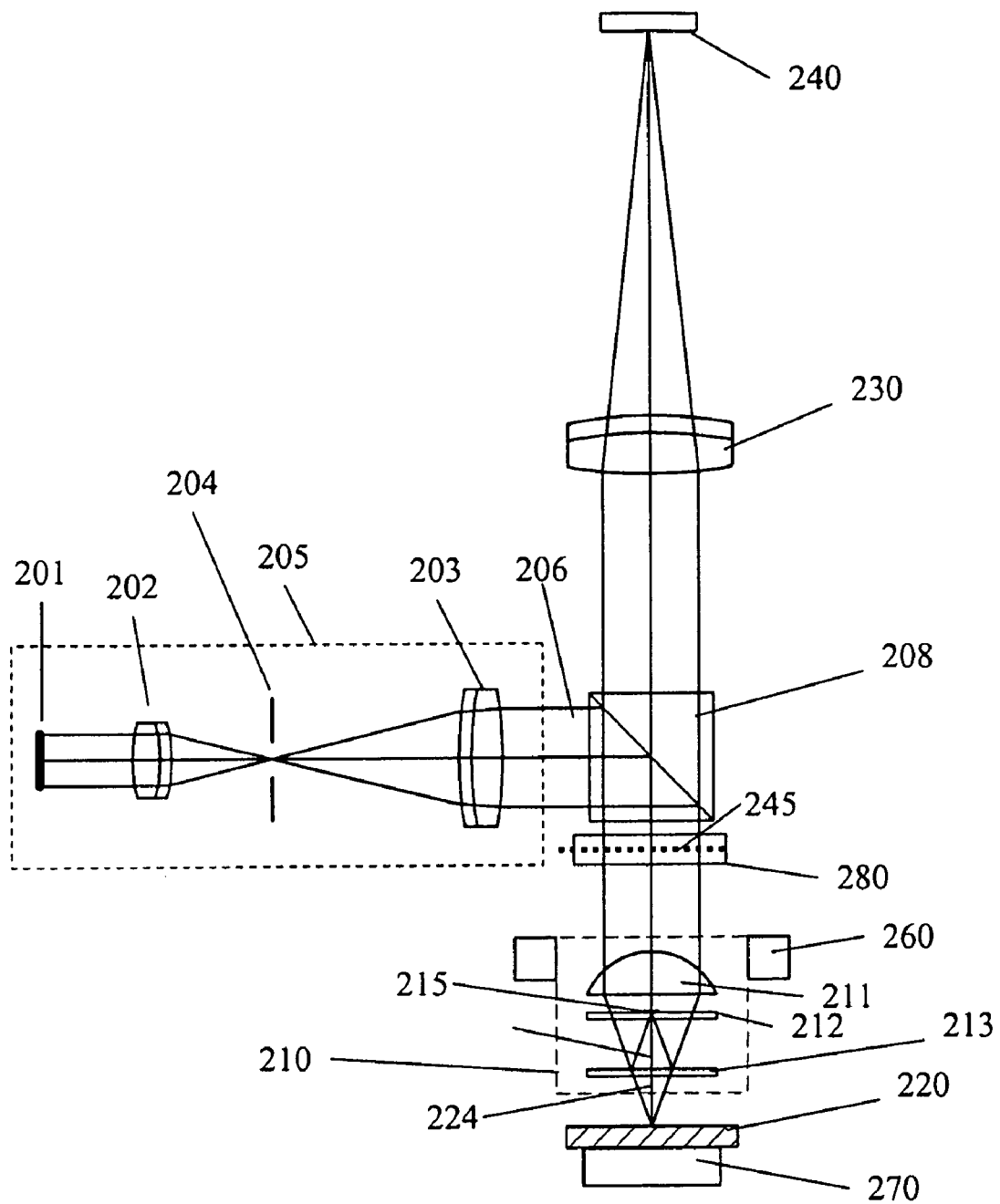
FIG. 11 is a schematic drawing of a Mirau-type, scanning interferometry system.

Referring to FIG. 11, a source module 205 provides illumination light 206 to a beam splitter 208, which directs it to a Mirau interferometric objective assembly 210. Assembly 210 includes an objective lens 211, a reference flat 212 having a reflective coating on a small central portion thereof defining a reference mirror 215, and a beam splitter 213. During operation, objective lens 211 focuses the illumination light towards a test sample 220 through reference flat 212. Beam splitter 213 reflects a first portion of the focusing light to reference mirror 215 to define reference light 222 and transmits a second portion of the focusing light to test sample 220 to define measurement light 224. Then, beam splitter 213 recombines the measurement light reflected (or scattered) from test sample 220 with reference light reflected from reference mirror 215, and objective 211 and imaging lens 230 image the combined light to interfere on detector (e.g., a multi-pixel camera) 240. As in the system of FIG. 1, the measurement signal(s) from the detector is sent to a computer (not shown).

The scanning in the embodiment of FIG. 11 involves a piezoelectric transducer (PZT) 260 coupled to Mirau interferometric objective assembly 210, which is configured to scan assembly 210 as a whole relative to test sample 220 along the optical axis of objective 211 to provide the scanning interferometry data I(ζ,h) at each pixel of the camera. Alternatively, the PZT may be coupled to the test sample rather than assembly 210 to provide the relative motion there between, as indicated by PZT actuator 270. In yet further embodiments, the scanning may be provided by moving one or both of reference mirror 215 and beam splitter 213 relative to objective 211 along the optical axis of objective 211.

Source module 205 includes a spatially extended source 201, a telescope formed by lenses 202 and 203, and a stop 204 positioned in the front focal plane of lens 202 (which coincides with the back focal plane of lens 203). This arrangement images the spatially extended to source onto the pupil plane 245 of Mirau interferometric objective assembly 210, which is an example of Koehler imaging. The size of stop controls the size of the illumination field on test sample 220. In other embodiments, the source module may include an arrangement in which a spatially extended source is imaged directly onto the test sample, which is known as critical imaging. Either type of source module may be used with the Linnik-type scanning interferometry system of FIG. 1.

In further embodiments, the scanning interferometer can be of the Michelson-type.

In further embodiments of the invention, the scanning interferometry system may used to determine angle-dependent scattering or diffraction information about a test sample, i.e., for scatterometry. For example, the scanning interferometry system may be used to illuminate a test sample with test light incident over only a very narrow range of incident angles (e.g., substantially normal incidence or otherwise collimated), which may then be scattered or diffracted by the test sample. The light emerging from the sample is imaged to a camera to interfere with reference light as described above. As with the reflected light in the embodiments described above, the spatial frequency of each component in the scanning interferometry signal will depend vary with angle of the test light emerging from the test sample. For substantially normal incidence, the spatial frequency varies according to:

$$K(\phi) = \frac{2\pi}{\lambda}\cos(\phi), \tag{12}$$

which differs from Eq. (4) be a factor of 2 because of the normal incidence. The other parts of the mathematical analysis remain unchanged, however, and the scanning interferometry data I(ζ,h) from a scattering or diffractive test sample can be analyzed according to Eqs. (7)-(10) to provide the angle-dependent, phase and amplitude scattering/diffraction coefficients for the test sample. Thus, a vertical scan (i.e., a scan along the optical axis of an objective) followed by Fourier analysis allows for a measurement of diffracted and/or scattered light as a function of emerging angle, without directly accessing or imaging the back focal plane of the objective. Moreover, as above, the angle-dependence of such optical properties can be determined locally over an area of the test sample based on the resolution of the imaging system and the camera pixel size. To provide the substantially normal incidence illumination, for example, the source module can be configured to image a point source onto the pupil plane or to otherwise decrease the degree to which the illumination light fills the numerical aperature of the measurement objective. The scatterometry technique may be useful for resolving discrete structures in the sample surface, such as grating lines, edges, or general surface roughness, which may diffract and/or scatter light to higher angles.

Figure 12:
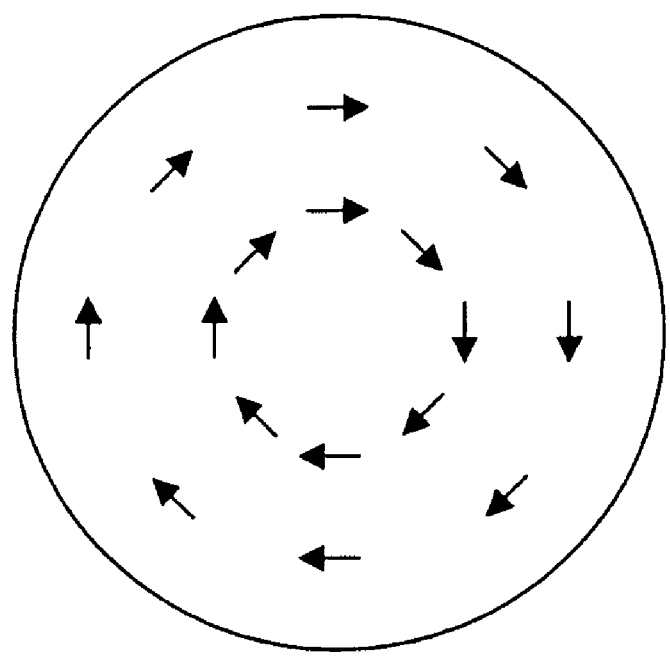
FIG. 12 is a diagram illustrating radial polarization in the pupil plane.

In the above embodiments, it has been assumed that the polarization state of the light in the pupil plane is random, i.e., comprised of approximately equal amounts of both s polarizations (orthogonal to the plane of incidence) and p (orthogonal to the plane of incidence) polarizations. Alternative polarizations are possible, including pure s polarization, such as may be realized by means of a radial polarizer placed in the pupil plane (e.g., in the back-focal plane of the measurement object in the case of a Linnik interferometer and in the back focal plane of the common objective in the Mirau interferometer). Such radial polarization is illustrated in FIG. 12. Other possible polarizations include radial p polarization, circular polarization, and modulated (e.g. two states, one following the other) polarization for ellipsometric measurements. In other words, optical properties of the test sample can be resolved not only with respect to their angle dependence, but also with respect to their polarization dependence or with respect to a selected polarization. Such information may also be used to improve the accuracy of thin film structure characterization.

To provide such ellipsometry measurements, the scanning interferometry system may include a fixed or variable polarizer in the pupil plane. Referring again to FIG. 11, the Mirau-type interferometry system, for example, includes polarization optics 280 in the pupil plane to select a desired polarization for the ligh incident on, and emerging from the test sample. Furthermore, the polarization optics may be reconfigurable to vary the selected polarization. The polarization optics may include one or more elements including polarizers, waveplates, apodization apertures, and/or modulation elements for selecting a given polarization. Furthermore, the polarization optics may be fixed, structured or reconfigurable, for the purpose of generating data similar to that of an ellipsometer. For example, a first measurement with a radially-polarized pupil for s polarization, followed by a radially-polarized pupil for p polarization. In another example, one may use an apodized pupil plane with linearly polarized light, e.g., a slit or wedge, which can be rotated in the pupil plane so as to direct any desired linear polarization state to the object, or a reconfigurable screen such as a liquid crystal display.

Moreover, the polarization optics may provide a variable polarization across the pupil plane (e.g., by including multiple polarizers or a spatial modulator). Thus, one can "tag" the polarization state according to spatial frequency, for example, by providing a different polarization for high angles of incidence than shallow angles.

In yet further embodiments, the selectable polarization may be combined with a phase shift as a function of polarization. For example, the polarization optics may include a linear polarizer is positioned in the pupil plane and followed by two waveplates (e.g., eighth-wave plates) in opposing quadrants of the pupil plane. The linear polarization results in a full range of polarization angles with respect to the incident planes of the objective. If the waveplates are aligned so that, for example, the predominately s-polarized light has a fixed phase shift, then both radial s polarized and p polarized light are present simultaneously, but shifted in phase with respect to each other, e.g., by pi, so that the interferometer is effectively detecting the difference between these two polarization states as the fundamental signal.

As described above, placing the polarization optics in the pupil plane allows for various angle-resolved type polarization measurements. In further embodiments, however, polarization optics may be positioned elsewhere in the apparatus. For example, linear polarization can be achieved anywhere in the system.

In further embodiments, any of the reflectometry, scatterometry, and ellipsometry techniques described above may be repeated sequentially for different wavelengths to provide the wavelength dependence of the sample optical properties of interest. Such information may be used for fitting more complex surface models.

Other embodiments of the invention may include broadband illumination. For example, the illumination may be broadband, as is common in, e.g., white light interference microscopes. This increases the amount of information to which the computer may find the best fit for a complex surface model.

The light source for the scanning interferometry systems may be any of, for example, a laser, a laser diode, a light-emitting diode, a filtered incandescent source, and an arc lamp.

The methods and systems described above can be particularly useful in semiconductor applications. Additional embodiments of the invention include applying any of the measurement techniques described above to address any of the semiconductor applications described below.

It is presently of considerable interest in the semiconductor industry to make quantitative measurements of surface topography. Due to the small size of typical chip features, the instruments used to make these measurements typically must have high spatial resolution both parallel and perpendicular to the chip surface. Engineers and scientists use surface topography measuring systems for process control and to detect defects that occur in the course of manufacturing, especially as a result of processes such as etching, polishing, cleaning and patterning.

For process control and defect detection to be particularly useful, a surface topography measuring system should have lateral resolution comparable to the lateral size of typical surface features, and vertical resolution comparable to the minimum allowed surface step height. Typically, this requires a lateral resolution of less than a micron, and a vertical resolution of less than 1 nanometer. It is also preferable for such a system to make its measurements without contacting the surface of the chip, or otherwise exerting a potentially damaging force upon it, so as to avoid modifying the surface or introducing defects. Further, as it is well-known that the effects of many processes used in chip making depend strongly on local factors such as pattern density and edge proximity, it is also important for a surface topography measuring system to have high measuring throughput, and the ability to sample densely over large areas in regions which may contain one or many surface features of interest.

It is becoming common among chip makers to use the so-called 'dual damascene copper' process to fabricate electrical interconnects between different parts of a chip. This is an example of a process which may be effectively characterized using a suitable surface topography system. The dual damascene process may be considered to have five parts: (1) an interlayer dielectric (ILD) deposition, in which a layer of dielectric material (such as a polymer, or glass) is deposited onto the surface of a wafer (containing a plurality of individual chips); (2) chemical mechanical polishing (CMP), in which the dielectric layer is polished so as to create a smooth surface, suitable for precision optical lithography, (3) a combination of lithographic patterning and reactive ion etching steps, in which a complex network is created comprising narrow trenches running parallel to the wafer surface and small vias running from the bottom of the trenches to a lower (previously defined) electrically conducting layer, (4) a combination of metal deposition steps which result in the trenches and vias being over-filled with copper, and (5) a final chemical mechanical polishing (CMP) step in which the excess copper is removed, leaving a network of copper filled trenches (and possibly vias) surrounded by dielectric material.

Typically the thickness of the copper in the trench areas (i.e., the trench depth), and the thickness of the surrounding dielectric lie in a range of 0.2 to 0.5 microns. The width of the resulting trenches may be in a range of from 100 to 100,000 nanometers, and the copper regions within each chip may in some regions form regular patterns such as arrays of parallel lines, and in others they may have no apparent pattern. Likewise, within some regions the surface may be densely covered with copper regions, and in other regions, the copper regions may be sparse. It is important to appreciate that the polishing rate, and therefore the remaining copper (and dielectric) thickness after polishing, depends strongly and in a complex manner on the polishing conditions (such as the pad pressure and polishing slurry composition), as well as on the local detailed arrangement (i.e., orientation, proximity and shape) of copper and surrounding dielectric regions.

This 'position dependent polishing rate' is known to give rise to variable surface topography on many lateral length scales. For example, it may mean that chips located closer to the edge of a wafer on aggregate are polished more rapidly than those located close to the center, creating copper regions which are thinner than desired near the edges, and thicker than desired at the center. This is an example of a 'wafer scale' process nonuniformity—i.e., one occurring on length scale comparable to the wafer diameter. It is also known that regions which have a high density of copper trenches polish at a higher rate than nearby regions with low copper line densities. This leads to a phenomenon known as 'CMP induced erosion' in the high copper density regions. This is an example of a 'chip scale' process nonuniformity—i.e., one occurring on a length scale comparable to (and sometimes much less than) the linear dimensions of a single chip. Another type of chip scale nonuniformity, known as 'dishing', occurs within single copper filled trench regions (which tend to polish at a higher rate than the surrounding dielectric material). For trenches greater than a few microns in width dishing may become severe with the result that affected lines later exhibit excessive electrical resistance, leading to a chip failure.

CMP induced wafer and chip scale process nonuniformities are inherently difficult to predict, and they are subject to change over time as conditions within the CMP processing system evolve. To effectively monitor, and suitably adjust the process conditions for the purpose of ensuring that any non-uniformities remain within acceptable limits, it is important for process engineers to make frequent non-contact surface topography measurements on chips at a large number and wide variety of locations. This is possible using embodiments of the interferometry techniques described above.

More generally, the interferometry techniques described above may used for any of the following surface analysis problems: simple thin films; multilayer thin films; sharp edges and surface features that diffract or otherwise generate complex interference effects; unresolved surface roughness; unresolved surface features, for example, a sub-wavelength width groove on an otherwise smooth surface; dissimilar materials; polarization-dependent properties of the surface; and deflections, vibrations or motions of the surface or deformable surface features that result in incident-angle dependent perturbations of the interference phenomenon. For the case of simple thin films, the variable parameter of interest may be the film thickness, the refractive index of the film, the refractive index of the substrate, or some combination thereof. For the case of dissimilar materials, for example, the surface may comprise a combination of thin film and a solid metal, and a fit of the angle-dependent surface properties would be made to a library of theoretical predictions which would include both surface structure types to automatically identify the film or the solid metal by a match to the corresponding interference intensity signal Any of the computer analysis methods described above can be implemented in hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

A number of embodiments of the invention have been described. Nevertheless, it will be understood that various modifications may be made without departing from the spirit and scope of the invention.

What is claimed is:

1. A method comprising:
   collecting test light emerging from a test object to interfere with reference light on a detector, wherein the test and reference light are derived from a common source;
   varying an optical path length difference from the source to the detector between interfering portions of the test and reference light;
   for each of multiple surface locations of the test object, calculating multiple functions based on an interference signal corresponding to the interference between the test light emerging from the corresponding surface location of the test object and the reference light as the optical path length difference is varied, wherein each function has a multi-valued output; and
   comparing the multi-valued output of each of the multiple functions for each of the surface locations to multi-valued information derived from a model to collectively determine a best-fit value for each of one or more model parameters and thereby yield information about the test object.

2. The method of claim 1, wherein the multiple functions comprise an amplitude function and a phase function.

3. The method of claim 2, where the amplitude and phase functions correspond to amplitude and phase components of a transform of the interference signal.

4. The method of claim 3, wherein the transform is a Fourier transform.

5. The method of claim 1, wherein the multiple functions are each functions of at least one coordinate comprising a spatial frequency coordinate.

6. The method of claim 5, wherein the spatial frequency coordinate has a one-to-one mapping to an angle coordinate for the test light emerging from the test object.

7. The method of claim 1, wherein the multiple functions are each functions of at least one coordinate comprising a wavelength coordinate.

8. The method of claim 1, wherein the test object comprises a layer and the one or more model parameters comprise a thickness for the layer.

9. The method of claim 1, wherein the test object comprises a grating and the one or more model parameter comprise a property of the grating.

10. The method of claim 1, further comprising outputting information about the best-fit values for the model parameters and wherein the test object is a component in a semiconductor manufacturing process and the method further comprises characterizing the semiconductor manufacturing process based on the information about the best fit values for the model parameters.

11. The method of claim 1, wherein the detector is a camera having multiple detector elements and the collecting comprises imaging the test light emerging from different locations of the test object to corresponding locations on the camera.

12. The method of claim 1, wherein the test light is collected over a range of angles that correspond to a numerical aperture of 0.75 or greater.

13. The method of claim 1, wherein the test light is collected over a range of angles that correspond to a numerical aperture greater than 0.7.

14. The method of claim 1, wherein the test light is collected over a range of angles that correspond to a numerical aperture greater than 0.9.

15. The method of claim 1, wherein the collecting further comprises polarizing the test light before interfering it with the reference light on the detector.

16. The method of claim 1, wherein the optical path length difference is varied over a range larger than a coherence length for an interferometry system used to measure the interference signal.

17. The method of claim 16, wherein the coherence length is based on a range of wavelengths and a range of collection angles for the test light.

18. The method of claim 1, wherein the calculating and comparing is repeated for each of multiple interference signals corresponding to different transverse locations of the test object.

19. An apparatus comprising:
a light source;
a detector;
a scanning interferometer configured to collect test light emerging from a test object to interfere with reference light on the detector, wherein the test and reference light are derived from the light source; and
an electronic processor coupled to the detector and the scanning interferometer, wherein the electronic processor is configured to:
i) cause the scanning interferometer to vary an optical path length difference from the source to the detector between interfering portions of the test and reference light;
ii) for each of multiple surface locations of the test object, cause the detector to measure at least one interference signal corresponding to the interference between the test light emerging from the corresponding surface location of the test object and the reference light as the optical path length difference is varied;
iii) for each of the multiple surface locations of the test object, calculate multiple functions based on the corresponding interference signal, wherein each function has a multi-valued output; and
iv) compare the multi-valued output of each of the multiple functions for each of the surface locations to multi-valued information derived from a model to collectively determine a best-fit value for each of one or more model parameters for the test object and thereby yield information about the test object.

20. The apparatus of claim 19, wherein the multiple functions comprise an amplitude function and a phase function.

21. The apparatus of claim 19, where the amplitude and phase functions correspond to amplitude and phase components of a transform of the interference signal.

22. The apparatus of claim 21, wherein the transform is a Fourier transform.

23. The apparatus of claim 19, wherein the multiple functions are each functions of at least one coordinate comprising a spatial frequency coordinate.

24. The apparatus of claim 23, wherein the spatial frequency coordinate has a one-to-one mapping to an angle coordinate for the test light emerging from the test object.

25. The apparatus of claim 19, wherein the multiple functions are each functions of at least one coordinate comprising a wavelength coordinate.

26. The apparatus of claim 19, wherein the processor is further configured to output information.

27. The apparatus of claim 19, wherein the detector is a camera having multiple detector elements and the interferometer is configured to image the test light emerging from different locations of the test object to corresponding locations on the camera.

28. The apparatus of claim 19, wherein the interferometer is configured to collect the test light over a range of angles that correspond to a numerical aperture of 0.75 or greater.

29. The apparatus of claim 19, wherein the interferometer is configured to collect the test light over a range of angles that correspond to a numerical aperture greater than 0.7.

30. The apparatus of claim 19, wherein the interferometer is configured to collect the test light over a range of angles that correspond to a numerical aperture greater than 0.9.

31. The apparatus of claim 19, wherein the interferometer is further configured to polarize the test light before interfering it with the reference light on the detector.

32. The apparatus of claim 19, wherein the interferometer is configured to vary the optical path length difference over a range larger than a coherence length for the interferometer.

33. The apparatus of claim 19, wherein the coherence length is based on a range of wavelengths and a range of collection angles for the test light.

34. The method of claim 19, wherein the electronic processor is further configured to perform the calculating and comparing for each of multiple interference signals corresponding to different transverse locations of the test object.

* * * * *